(12) United States Patent
Kim et al.

(10) Patent No.: US 8,026,414 B2
(45) Date of Patent: Sep. 27, 2011

(54) MOLECULAR MARKER ASSOCIATED WITH CMV RESISTANCE AND USE THEREOF

(75) Inventors: Shinje Kim, Gyeonggi-do (KR); Ju-Kwang Hwang, Chungcheongbuk-do (KR); Goon-Bo Kim, Gyeonggi-do (KR); Su Kim, Chungcheongbuk-do (KR)

(73) Assignee: FNP Corp., Ltd., Cheongju, Chungcheongbuk-Do (KR)

( * ) Notice: Subject to any disclaimer, the term of this patent is extended or adjusted under 35 U.S.C. 154(b) by 1419 days.

(21) Appl. No.: 10/577,433

(22) PCT Filed: Oct. 27, 2004

(86) PCT No.: PCT/KR2004/002732
§ 371 (c)(1),
(2), (4) Date: Apr. 27, 2006

(87) PCT Pub. No.: WO2005/040426
PCT Pub. Date: May 6, 2005

(65) Prior Publication Data
US 2010/0199390 A1 Aug. 5, 2010

(30) Foreign Application Priority Data
Oct. 27, 2003 (KR) .................... 10-2003-0075272

(51) Int. Cl.
*A01H 5/00* (2006.01)
*A01H 5/10* (2006.01)
*C12N 15/09* (2006.01)
*C12N 15/82* (2006.01)
*C12N 15/29* (2006.01)
*C12Q 1/60* (2006.01)
*C12Q 1/70* (2006.01)

(52) U.S. Cl. ........ 800/301; 800/278; 800/279; 800/295; 800/298; 800/306; 800/307; 800/308; 800/314; 800/323; 800/317.3; 435/5; 435/69.1; 435/468; 435/419; 435/6.1; 536/23.6; 536/24.33

(58) Field of Classification Search ................ None
See application file for complete search history.

(56) References Cited

U.S. PATENT DOCUMENTS

| 6,262,343 B1 * | 7/2001 | Staskawicz et al. .......... 800/279 |
| 6,337,071 B1 * | 1/2002 | Molyneux ..................... 424/745 |
| 6,342,655 B1 | 1/2002 | Boeshore et al. |

FOREIGN PATENT DOCUMENTS

| JP | 2-167080 | 6/1990 |
| WO | WO 0177384 | * 10/2001 |

OTHER PUBLICATIONS

Bharti et al. Accession No. CG834049, Deposited Nov. 12, 2003.*
Kalantidis et al., "The Occurrence of CMV-Specific Short RNAs in Transgenic Tobacco Expressing Virus-Derived Double-Stranded RNA is indicative of Resistance to the Virus," *Molecular Plant-Microbe Interactions*, 2002, vol. 15, No. 8, pp. 826-833, The American Phytopathological Society, St. Paul, Minnesota, U.S.A.
Shin et al., "The potential use of a viral coat protein gene as a transgene screening marker and multiple virus resistance of pepper plants coexpressing coat proteins of cucumber mosaic virus and tomato mosaic virus," *Transgenic Research*, 2002, vol. 11, pp. 215-219, Kluwer Academic Publishers, the Netherlands.
Glenn et al., "Molecular characterization of FDB1 and FDB2, two Fusarium verticillioides genes essential for detoxification of maize antimicrobial compounds," *Phytopathology*, 2003, vol. 93, n. 6, p. S29, The American Phytopatholotgical Society, St. Paul, Minnesota, U.S.A.—(Abstract Only—APS Abstracts of Presentations—2003 APS Annual Meeting).

* cited by examiner

*Primary Examiner* — Medina A Ibrahim
(74) *Attorney, Agent, or Firm* — Buchanan Ingersoll & Rooney PC

(57) ABSTRACT

The present invention relates to a cucumber mosaic virus (CMV) resistance-associated molecular marker and the use thereof, and more particularly to a nucleic acid consisting of nucleotide sequence having a very high association with the CMV-resistant character of plants, a primer comprising a partial nucleotide sequence of the nucleic acid, and a method for detecting CMV-resistant plants using the nucleic acid or the primer. The inventive molecular marker has advantages in that it can detect CMV-resistant plants in a rapid and precise manner without inoculating CMV directly into plants, and also can determine the genotype of CMV-resistant plants.

14 Claims, 8 Drawing Sheets

Plant sample: $R_0 R_1 S_0 S_1$    F2 marker test:       R R S S R R R R R R R R R R R R R R R R R R R R
pathological test: R R S S R R R R R R R R R R R R R R R R R R R R

F2 marker test:       R R R R R R R R R R R R R R R R R R R R R R R R
pathological test: R R R R R R R R R R R R R R R R R R R R R R R R marker test:       R R R R R R R R R R R S S S S S S S S S S S
pathological test: R R R R R R R R R R R S S S S S S S S S S S marker test:       R R R R R R R R R R R S S S S S S S S S S S
pathological test: R R R R R R R R R R R S S S S S S S S S S S

SEQUENCE LISTING

<160> NUMBER OF SEQ ID NOS: 28

<210> SEQ ID NO 1
<211> LENGTH: 10
<212> TYPE: DNA
<213> ORGANISM: Artificial Sequence
<220> FEATURE:
<223> OTHER INFORMATION: RAPD primer (OPC-O7)

<400> SEQUENCE: 1
gtcccgacga                                                              10

<210> SEQ ID NO 2
<211> LENGTH: 1027
<212> TYPE: DNA
<213> ORGANISM: Capsicum annuum

<400> SEQUENCE: 2
gacataatgt gtgactatga gtagtagggt acggactcat agggccaata gtatggatgg        60
cttgtgacat tgcccagaca acaagtcatg gtgacaactc gtartcagtc ttarcgagtc       120
ttcatgtaac ccgtagcgac taggcggtag attttagct tacatttaag gcatcttact        180
aatttctctc tttcccaaca aaatacccc gacatataac acattgggga ccctatttc        240 ataactttaa caatcaatga cacctchtaa ccccttaaa ytccccactc aaaggcaaga       300
ctagggtttc aagaaattgg tcatctaggg ctctacgagt gatttcttct tcaaatttct       360
tggggattaa ggcatgtatc tctatcccta aacttttttt tcattatgta attaattggt      420
ttattattca catggttttg atgttgggtt tagcatgatg ggttgagtgt tttggatgta      480
atttgtttaa atgcttttcc cttgcttatt atggaataat tttatttgaa ttgatgatta      540
gtaaaatcat ttgggtgctt gggaatggtg aatgaaatag ggggtacaag gattccctaa      600
atttgtaaac aatggaaata gggggttcaag gatcacccaa ataattggat ttttgaataa    660 ttggatttt gtattgaaat tgataagaac ctcaacacac ttgcataatt ggttytagaa       720
tgtgattaat taatttctca ggcctacttt cttaraatta rcgcattgca taagaggata    780
acatayaaga atgatcttaa aaacgttgtg aggtacaagg attcacctaa gtgaatgatt      840
tttcttgaaa accttgtgcg gtacaaggat tctccaaagt gtatgataaa tggagtttgg      900
gtgtacaagg attcttccaa gtaatggatt aattgaattt ctagtaagat ttagtcagta    960
tgacgatgcc acttcataat gccttactta tgtttcagac tatctttcga attcttcttt   1020
tgggcta                                                                1027

<210> SEQ ID NO 3
<211> LENGTH: 21
<212> TYPE: DNA
<213> ORGANISM: Artificial Sequence
<220> FEATURE:
<223> OTHER INFORMATION: CRSCC07a primer for inverse PCR

<400> SEQUENCE: 3
gtcccgacga tagcccaaaa g                                                 21

<210> SEQ ID NO 4
<211> LENGTH: 20
<212> TYPE: DNA
<213> ORGANISM: Artificial Sequence
<220> FEATURE:
<223> OTHER INFORMATION: CRINVR65 primer for inverse PCR

```
<400> SEQUENCE: 4
ttggccctat gagtccgtac                                           20

<210> SEQ ID NO 5
<211> LENGTH: 20
<212> TYPE: DNA
<213> ORGANISM: Artificial Sequence
<220> FEATURE:
<223> OTHER INFORMATION: CRINVR125 primer for inverse PCR

<400> SEQUENCE: 5
actgactacg agttgtcacc                                           20

<210> SEQ ID NO 6
<211> LENGTH: 20
<212> TYPE: DNA
<213> ORGANISM: Artificial Sequence
<220> FEATURE:
<223> OTHER INFORMATION: CRINVF629 primer for inverse PCR

<400> SEQUENCE: 6 tagggggttca aggatcaccc                                          20

<210> SEQ ID NO 7
<211> LENGTH: 20
<212> TYPE: DNA
<213> ORGANISM: Artificial Sequence
<220> FEATURE:
<223> OTHER INFORMATION: CRINVR796 primer for inverse PCR

<400> SEQUENCE: 7
tatcctctta tgcaatgcgc                                           20

<210> SEQ ID NO 8
<211> LENGTH: 20
<212> TYPE: DNA
<213> ORGANISM: Artificial Sequence
<220> FEATURE:
<223> OTHER INFORMATION: CRINVR840 primer for inverse PCR

<400> SEQUENCE: 8
aatccttgta cctcacaacg                                           20

<210> SEQ ID NO 9
<211> LENGTH: 20
<212> TYPE: DNA
<213> ORGANISM: Artificial Sequence
<220> FEATURE:
<223> OTHER INFORMATION: CRINVF975 primer for inverse PCR

<400> SEQUENCE: 9
cgatgccact tcataatgcc                                           20

<210> SEQ ID NO 10
<211> LENGTH: 20
<212> TYPE: DNA
<213> ORGANISM: Artificial Sequence
<220> FEATURE:
<223> OTHER INFORMATION: Inv 1030514 R primer for inverse PCR

<400> SEQUENCE: 10
gacttgggca ctacactgga                                           20

<210> SEQ ID NO 11
<211> LENGTH: 20
<212> TYPE: DNA
```

```
<213> ORGANISM: Artificial Sequence
<220> FEATURE:
<223> OTHER INFORMATION: Inv 1030514 F primer for inverse PCR

<400> SEQUENCE: 11
acataggcgt gtgctctgga                                                  20

<210> SEQ ID NO 12
<211> LENGTH: 21
<212> TYPE: DNA
<213> ORGANISM: Artificial Sequence
<220> FEATURE:
<223> OTHER INFORMATION: CR 1541-3 primer for inverse PCR

<400> SEQUENCE: 12
ggagtttcat catatgaagc c                                                21

<210> SEQ ID NO 13
<211> LENGTH: 22
<212> TYPE: DNA
<213> ORGANISM: Artificial Sequence
<220> FEATURE:
<223> OTHER INFORMATION: InvXbTopF1010 primer for inverse PCR

<400> SEQUENCE: 13
ggttcaagga tcacccaaat aa                                               22

<210> SEQ ID NO 14
<211> LENGTH: 22
<212> TYPE: DNA
<213> ORGANISM: Artificial Sequence
<220> FEATURE:
<223> OTHER INFORMATION: InvXbTopR107 primer for inverse PCR

<400> SEQUENCE: 14
ttcaccttag tccccaaacc ta                                               22

<210> SEQ ID NO 15
<211> LENGTH: 20
<212> TYPE: DNA
<213> ORGANISM: Artificial Sequence
<220> FEATURE:
<223> OTHER INFORMATION: EV Inver F2 primer for inverse PCR

<400> SEQUENCE: 15
aacccaagcc tattttagcc                                                  20

<210> SEQ ID NO 16
<211> LENGTH: 22
<212> TYPE: DNA
<213> ORGANISM: Artificial Sequence
<220> FEATURE:
<223> OTHER INFORMATION: EV-INV-XbaI primer for inverse PCR

<400> SEQUENCE: 16
ggtaataggg ttcaccttag tc                                               22

<210> SEQ ID NO 17
<211> LENGTH: 20
<212> TYPE: DNA
<213> ORGANISM: Artificial Sequence
<220> FEATURE:
<223> OTHER INFORMATION: CRINVF5095 primer for inverse PCR

<400> SEQUENCE: 17
ctttgagcca aagaatggaa                                                  20
```

```
<210> SEQ ID NO 18
<211> LENGTH: 20
<212> TYPE: DNA
<213> ORGANISM: Artificial Sequence
<220> FEATURE:
<223> OTHER INFORMATION: CRINVR4776 primer for inverse PCR

<400> SEQUENCE: 18
tttggtaatg accggagacc                                                   20

<210> SEQ ID NO 19
<211> LENGTH: 20
<212> TYPE: DNA
<213> ORGANISM: Artificial Sequence
<220> FEATURE:
<223> OTHER INFORMATION: INVER0827R primer for inverse PCR

<400> SEQUENCE: 19
atagcagagg agcaccctac                                                   20

<210> SEQ ID NO 20
<211> LENGTH: 22
<212> TYPE: DNA
<213> ORGANISM: Artificial Sequence
<220> FEATURE:
<223> OTHER INFORMATION: INVER0827F1 primer for inverse PCR

<400> SEQUENCE: 20
ggtacaagga ttccccaaag tg                                                22

<210> SEQ ID NO 21
<211> LENGTH: 25
<212> TYPE: DNA
<213> ORGANISM: Artificial Sequence
<220> FEATURE:
<223> OTHER INFORMATION: INVER0827F2 primer for inverse PCR

<400> SEQUENCE: 21
gatttagtca gtatgacgat gccac                                             25

<210> SEQ ID NO 22
<211> LENGTH: 5591
<212> TYPE: DNA
<213> ORGANISM: Capsicum annuum

<400> SEQUENCE: 22
tctagaacta gccagttcat gaggctcaat cctctgacct ttactagctc taaggtttag        60
gaggatcctc aaaggttcat gtatgagata gaaaaaacat ttagagtgat acatgctttc       120
gactctgaag gtgtataatt ttcaaaatat cagctgaagg atgtggtata tcaatgtat        180 gagaagtagg agcagttgag gggggatgat gctgagttag tcatatggga tattttccta       240
gtacctttct tgattattc tttcctcagg agataaggaa agcaaatgct gaggagttta        300
tgaataactt gataagggtt tgatccaccc tagtatttct ctgtagggtg ctcctctgct       360
atttatttgt tagaaagatg gttccctta gatgtgtata gattatcgct agttgaataa       420
ggtgactatg aagaaaaagt accctctccc taagattgat gatttattca tccagcttca      480
gggtgcaaag tactttccta aaattaatct ctgttaaggt tattattagt tgaaaattag      540
ggatgtggat atccctaagg ctactttca aacccagtgt ggtcattatg agttttggt        600 gatgtcctat ggtttgacta atgctccggt ggcaatcaag gatcttatga acatagtatt      660
ctgttagttc ctggatttat ttgttattgt gttaatagat gatattttgg tatattctaa      720
```

```
gagcgaggct gatcacgccg atcatctcca tatagtattg caaactttta aagatcaact     780
gttgtacgcc aaattttcta agtgtgaatt atggttgaat gtggtgacct tccttggtta     840
tattatttct agtgagggga ttatggtgga tccacaaaaa ttttatgcgg tgaagaagtg     900
gcctaaaacc atgattccaa ccaatattta gagttttttgg gtttagttag atattatagg    960
aggtttgtgg agagtttctc atcaattgat gctctattta ttaagttaac tcagaaaaaa    1020
ggtatggttt ctatggtcca atgcttgtca gggtagcttt gataagttga aggataagtt    1080
gactttggat atgatcttga ccctacccga aggttttaat gttttttttaa ttttgatgca   1140
tcccgtgtag gacttggttg tgttttgatg tagaaacaat agggttctgg cctatgcttc    1200
taggaaattg aaagttcatg aaatgaatta tgcgacacat aacttagaat tattagttgt    1260
ggtattttca ttgaagctta ggtatcgtta tttgtatggg ttcatgttga tatatgtttt    1320
gatcataaga ttctgtagta tgtgttcacc cagaaggagt tgaatctcag gcaaaggaca    1380
tggcttgagt ttctcaaagg ctatgacatt agtctccatt acaacccagg taaatctaac    1440
atggttgttg gtattcttag taggttgtcc atgggaagat tataaaatat ggatgaggaa    1500
aaatgagatt tggtgaagta tattcaccga ttttggtaacc ttggagttcg tcttttggat   1560
tctgaggatg gaggtatggt tgttcaagag gtggtgaagt catctcttag tgttgaagta    1620
aaagcgaaac atgtcttgga tcctatctta atgcaaatca aagatgatgt gggtcaacag    1680
aaggttatgg ccttcaagat tggtagtaat ggtattttaa ggtaccaagg tagattgtgt    1740
gttaccgatg ttaatgggtt atgagaatga atttttggttg aagctcatga gtcgtgattt   1800
atggctcatc ttggtttgac gaagatgtac catgattcga aggagattta ttggttgaat    1860
aatatgaaga gagatgtggc aaattttgtt gctatgttca tggtttgcca acaagtgaag    1920
gtggggaacc taaggcctgg tggattctat cgctcgtgtg aagtgagag gtaatcagta     1980
tggattttgt ttccagtctt ccacggtctc gtagtaaatt ttatttgatt tgggtcatca    2040
ttgataggat gtctaagtct actcacttct tgccagtgag gactaataat tcatgggagg    2100
actacgcgaa gttttcatt caggatatca tcaagttgca tggtgcttta gtttctatta    2160
tatctgatcg aggtactcag ttctcgtcta acttttagtg attatttcat gtaggtttgg    2220
ggactaaggt gaaccctatt accatttttcc acccacagaa agatgtacaa gcagagagga   2280
ctattcagac tttggatagt atgctaaagg tatttgtgat taacttttgt ggtatttggg    2340
tttaccatat gcctctctta ctgtttgtgt ataataacaa ctattattct agcattcaga    2400
tgccccgttt gaggctttgg atggtaggag atgtcgttct cctattgggt ggttcaaatt    2460
tggtaagact agattggtca gcctggactt tgttcatgaa gctatagata aggtgaaggt    2520
gattaggat attcttaata ccacccaatg tcaccaaaat tcctatgtag acgtgaggca     2580
aagagagtta gagtttgatg ttggcaatta ggtgctcttg aaaatatccc ccatgaagga    2640
tgtgatatga tttgggaaga agcggaagct cagtcctcgt tatgtttgct cgtacttgaa    2700
ccttaggaga gtgggttatg ttgtttatga tttggatttg cctcgtagtt tgggttccat    2760
tcacctggag ttccacgtgt tgatgttgaa gaagtgcatg ggtgatcctt ccttgattgt    2820
ccttttgggg agtgttggta tttcatattc cttgtcttat gaggtattcc tgattgagat    2880
tttggatagg aaagtctatc atttgaggaa taaggatgtg gcttcgatga atgttctatt    2940
gaggaatcat aaggttgaag aagctacttg ggaagctaaa gaggacatga agtccaaata    3000
tccattcttg ttccctattc cggatagttg ctctcaagtt atgtgttttc cttaacatat    3060
ttgtatttg actttgttaa aggaaagtgt ggttgtgttt tgtgttaaat catacaaatg     3120
```

```
gatgctctgt ctcattattc agggacgaat aatcctacgg ggggggggggg gggaatgtaa    3180
cacctcagat ttttggtcct tggaaaattt tttgactttt gaacttacag cctatgcaat    3240
gactcatctc acgagtcgta aggtgttgtc ttggcaggtc gtaggacccc aatcatagga    3300
tgaccagtaa agcttttttca tgatactggc ttggtgatga cttgcacccc actagttgta    3360
aagattcatt acgagtcgta atatccagat cataggtgtt ccaatgaaat ttgtcttttc    3420
tactctcttg attaaactag acataatgag tctaatacac tcttaacaag tcattgtgtg    3480
cctttcctgg caaatccagt gtagtgccca agtcattctt ccttgactat aactgaaccc    3540
gacgagacat aatgtgtgac tatgagtagt agggtacgga ctcataggc caatagtatg    3600
gatggcttgt gacattgccc agacaacaag tcatggtgac aactcgtagt cagtcttagc    3660
gagtcttcat gtaacccgta gcgactaggc ggtagatttt tagcttacat ttaaggcatc    3720
ttactaattt ctctctttcc caacaaaata cccccgacat ataacacatt ggggacccta    3780
ttttcataac tttaacaatc aatgacacct cttaaccccc ttaaattccc cactcaaagg    3840
caagactagg gtttcaagaa attggtcatc tagggctcta cgagtgattt cttcttcaaa    3900
tttcttgggg attaaggcat gtatctctat ccctaaactt ttttttcatt atgtaattaa    3960
ttggtttatt attcacatgg ttttgatgtt gggtttagca tgatgggttg agtgttttgg    4020
atgtaatttg tttaaatgct ttccccttgc ttattatgga ataattttat ttgaattgat    4080
gattagtaaa atcatttggg tgcttgggaa tggtgaatga aataggggta caaggattcc    4140
ctaaatttgt aaacaatgga aatagggggtt caaggatcac ccaaataatt ggattttga    4200
ataattggat ttttgtattg aaattgataa gaaccctcaac acacttgcat aattggttct    4260
agaatgtgat taattaattt tctaggccta cttttcttaga attagcgcat tgcataagag    4320
gataacatac aagaatgatc ttaaaaacgt tgtgaggtac aaggattcac ctaagtgaat    4380
gatttttctt gaaaaccttg tgcggtacaa ggattcccca aagtgtatga taaatgagt    4440
ttgggtgtac aaggattctt ccaagtaatg gattaattga atttctagta agatttagtc    4500
agtatgacga tgccacttca taatgcctta cttatgtttc agactatctt tcgaattctt    4560
cttttgggct atcgtcgggg gcatgtccaa actttgattg attttggtt ctatttagag    4620
gatttgtgga tttctatgga ttgggatggt attattgatg catagaactt tccctatttt    4680
gaatttctct atcttgttat attttgaaa ttcatccact actagctgtg ttgtgttcta    4740
tttggctagg caaaaagggg tggtctccgg tcattaccaa acttgggaga cccttcatgg    4800
ccaggccctg gtttgggtca tgatattttc aacctcaaac aaaaatccat tctgaccatg    4860
agcacgattg attccacatc tttcatttga atattaatga tctttcaact ctagcaacac    4920
caattaagat acaaacatag gcgtgtgctc tggagagctc ctgaggttta ttttttagtg    4980
catacttatt tgtcattttt ccttaataca tctttttaaa tctataatgg cttcatatga    5040
tgaaactcca caagctatgg ataacaatgc ttcaaacaca atcttagcca taattgaatc    5100
cttgagccaa agaatggaaa gcttggaaag ctacttaaca aggaggatgt aaaacttgga    5160
aggccgttta gattccacca actcaacccc tcaaacctat aatgcttata ctagtggaca    5220
tactcaaaat atttccgcta cgatattcct agaaaccctc caccaaatgt acattcctca    5280
accacaaacc catgaaccca tcacacaaac cactacttat ccacaaaatt taaatctcat    5340
tagcccacta caacctcaat tcaaccaaga agaccacaaa accaagaacc agccatctaa    5400
ttaccctaaa ataaaggact accccaagct ccacttaagc aaaatccact aacccaagcc    5460
tattttagcc aaaataaaca catccaagtt gaagatataa aggaagaggg atctcaagga    5520
```

-continued

```
gaaaatgaag tgatggatga ggtggttgat aattattgaa ttgaaatatt taatatgtgc    5580
aagatatcga t                                                         5591

<210> SEQ ID NO 23
<211> LENGTH: 21
<212> TYPE: DNA
<213> ORGANISM: Artificial Sequence
<220> FEATURE:
<223> OTHER INFORMATION: SCC07S3 primer

<400> SEQUENCE: 23
gtagtagggt acggactcat a                                              21

<210> SEQ ID NO 24
<211> LENGTH: 21
<212> TYPE: DNA
<213> ORGANISM: Artificial Sequence
<220> FEATURE:
<223> OTHER INFORMATION: SCC07a primer

<400> SEQUENCE: 24
gtcccgacga tagcccaaaa g                                              21

<210> SEQ ID NO 25
<211> LENGTH: 21
<212> TYPE: DNA
<213> ORGANISM: Artificial Sequence
<220> FEATURE:
<223> OTHER INFORMATION: CR1541-3 primer

<400> SEQUENCE: 25
ggagtttcat catatgaagc c                                              21

<210> SEQ ID NO 26
<211> LENGTH: 20
<212> TYPE: DNA
<213> ORGANISM: Artificial Sequence
<220> FEATURE:
<223> OTHER INFORMATION: FP5416R primer

<400> SEQUENCE: 26
agtggagctt ggggtagtcc                                                20

<210> SEQ ID NO 27
<211> LENGTH: 15
<212> TYPE: DNA
<213> ORGANISM: Artificial Sequence
<220> FEATURE:
<223> OTHER INFORMATION: SCC07S3-change primer

<400> SEQUENCE: 27
ggtagtaggg tacgg                                                     15

<210> SEQ ID NO 28
<211> LENGTH: 15
<212> TYPE: DNA
<213> ORGANISM: Artificial Sequence
<220> FEATURE:
<223> OTHER INFORMATION: CR1541-3-change primer

<400> SEQUENCE: 28
gggagtttca tcagc                                                     15
```

US 8,026,414 B2

MOLECULAR MARKER ASSOCIATED WITH CMV RESISTANCE AND USE THEREOF

TECHNICAL FIELD

The present invention relates to a cucumber mosaic virus (CMV) resistance-associated molecular marker and the use thereof, and more particularly to a nucleic acid consisting of nucleotide sequences having a very high association with the CMV-resistant character of plants, a primer comprising a portion of the nucleotide sequence of the nucleic acid, and a method for detecting CMV-resistant plants using the nucleic acid or the primer.

BACKGROUND ART

Cucumber Mosaic Virus (hereinafter, referred to as "CMV") is a plant-pathogenic virus having the widest host range of plant viruses, and causes great economic damage to about 900 kinds of dicotyledonous and monocotyledonous plants in the whole world. Plants infected with CMV show mosaic symptoms on leaves, stems and fruits. Particularly, the affected leaves become smaller in size and crumpled, and show lesions along leaf veins. Also, the affected fruits show dark-green mosaic patterns and become uneven, thus reducing product quality.

Meanwhile, in order to breed a disease-resistant variety, a disease-resistant factor should be introduced by successive backcrossing from other varieties having the factor. In each of the introduction steps, the disease-resistant factor should be selected through a resistance test, and in this selection step, the use of a molecular marker having a close association with the disease-resistant factor will make the selection very convenient. Thus, methods for the diagnosis of CMV using the molecular marker and various technologies for the development of CMV-resistant varieties by transformation have been developed. For example, Korean Patent Application No. 2000-0025699 discloses the nucleotide sequence of a set of gene amplification primers for the diagnosis of cucumovirus, in which the primer set allows the diagnosis of CMV, peanut stunt virus and tomato aspermy virus, which belong to the cucumovirus group, as well as a method for the diagnosis and identification of genes using the primers. Also, Korean Patent Registration No. 0293567 discloses a method for developing CMV-resistant tomato lines, which comprises transforming tomatoes with a CMV coat protein gene isolated in Korea. Furthermore, Korean Patent Application No. 1993-0029605 discloses a hammerhead-type ribozyme which attacks the RNA of a CMV coat protein gene, in order to produce transgenic crops having resistance to CMV causing diseases in crops.

As described above, the prior art on the diagnosis of CMV resistance and on the development of CMV-resistant plants targets the CMV coat protein gene, and there is no report of the development of technology concerning a CMV-resistant factor which is inherent in plants.

Accordingly, there has been an urgent need for the development of a CMV resistance-associated molecular marker from plant lines having the CMV-resistant factor and for the development of a method for diagnosing CMV infection in plants using the developed molecular marker.

DISCLOSURE OF THE INVENTION

Therefore, the present invention has been made to satisfy the above-mentioned need, and it is an object of the present invention to provide a molecular maker consisting of nucleotide sequences having a very high association with a CMV-resistant character, and the use thereof.

To achieve the above object, in one aspect, the present invention provides an isolated nucleic acid consisting of a nucleotide sequence set forth in SEQ ID NO: 2 or SEQ ID NO: 22.

In another aspect, the present invention provides a primer for the detection of CMV-resistant plants, which comprises consecutive nucleotides selected from a nucleotide sequence set forth in SEQ ID NO: 2 or SEQ ID NO: 22.

In still another aspect, the present invention provides a kit for detection of CMV-resistant plant, which comprises the nucleic acid or the primer.

In yet another aspect, the present invention provides a method for detecting a CMV-resistant plant and a method for determining the genotype of the plant, the methods comprising analyzing the genomic DNA of a plant in the presence of the nucleic acid or the primer.

The further another aspect, the present invention provides a CMV-resistant plant which reproduce asexually by tissue culture and comprises a nucleic acid consisting of a nucleotide sequence shown SEQ ID NO: 2 or SEQ ID NO: 22, as well as a seed obtained therefrom.

Hereinafter, the present invention will be described in detail.

The present invention provides a molecular marker having a high association with the CMV-resistant character of plants (hereinafter, referred to as "a CMV resistance-associated molecular marker"). The CMV resistance-associated molecular marker provided in the present invention comprises a nucleic acid consisting of a nucleotide sequence set forth in SEQ ID NO: 2 or SEQ ID NO: 22. The nucleic acid includes RNA, DNA and cDNA, and preferably means DNA. The inventive molecular marker consists of nucleotide sequences having a close association with a CMV-resistant character, and is placed significantly close to the CMV-resistant gene. For this reason, the use of any polymorphism shown by the nucleotide sequence allows the presence or absence of the CMV resistance in plants to be determined.

Also, the inventive molecular marker comprises a primer for the detection of CMV-resistant plants, which comprises a series of nucleotides selected from the nucleotide sequence of the nucleic acid. The primer may preferably have at least 10 consecutive nucleotides, and more preferably at least 12 consecutive nucleotides, which are selected from the nucleotide sequence set forth in SEQ ID NO: 2 or SEQ ID NO: 22. The inventive primer can be so designed that it is suitable for various DNA polymorphism analyses known in the art, such as RFLP (restriction fragment length polymorphism), RAPD (randomly amplified polymorphic DNA), DAF (DNA amplification fingerprinting), AP-PCR (arbitrarily primed PCR), STS (sequence tagged site), EST (expressed sequence tag), SCAR (sequence characterized amplified regions), ISSR (inter-simple sequence repeat amplification), AFLP (amplified fragment length polymorphism), CAPS (cleaved amplified polymorphic sequence), PCR-SSCP (single-strand conformation polymorphism) and the like (Jordan et al., *Theor. Appl. Genet.*, 106:559-567, 2003; Martins M., R. et al., *Plant Cell Reports*, 22:71-78, 2003; Williams, J. G. K. et al., *Nucl. Acids Res.*, 18:6531-6535, 1990; Michelmore, R. W., et al., *Proc. Natl. Acad. Sci.* USA. 88:9828-9832, 1991; Martins et al., *Plant Cell Rep.*, 22:71-79, 2003; Orita et al., *Proc. Natl. Acad. Sci.* USA 86:2766-2770, 1989). For the DAF analysis, a primer consisting of 5-8 consecutive nucleotides can be designed and used. For example, a primer for the STS analysis can be so designed that it coincides with the terminal nucleotide sequence of an RFLP marker, and a primer for the SCAR analysis can be designed based on the terminal nucleotide sequence of an RAPD marker. Also, a primer for the CAPS analysis can be so designed that it contains a suitable restriction site. Preferably, the primer provided in the present invention may have a nucleotide sequence selected from the group consisting of SEQ ID NO: 1 and SEQ ID NO: 23 to SEQ ID NO: 26. Furthermore, the inventive primer may have modifications (e.g., additions, deletions and/or substitutions) if the modifications have no effect on the detection of polymorphism associated with a CMV-resistant character. Preferably, the inventive primer can be modified by making an addition and/or substitution of any base in at least 12 consecutive nucleotides selected from the nucleotide sequence set forth in SEQ ID NO: 2 or SEQ ID NO: 22. For example, the inventive primer may have a nucleotide sequence of SEQ ID NO: 27 or SEQ ID NO: 28.

The inventive molecular marker can be very useful for the detection of CMV-resistant plants. Thus, the present invention provides a method for the detection of a CMV-resistant plant, which comprises analyzing the genomic DNA of a plant in the presence of the nucleic acid or the primer. This method may be performed using various DNA polymorphism analyses known in the art. Example of the DNA polymorphism analyses which can be used in the present invention include, but are not limited to, RFLP (restriction fragment length polymorphism), RAPD (randomly amplified polymorphic DNA), DAF (DNA amplification fingerprinting), AP-PCR (arbitrarily primed PCR), STS (sequence tagged site), EST (expressed sequence tag), SCAR (sequence characterized amplified regions), ISSR (inter-simple sequence repeat amplification), AFLP (amplified fragment length polymorphism), CAPS (cleaved amplified polymorphic sequence), PCR-SSCP (PCR-single strand conformation polymorphism) and the like (Jordan et al., *Theor. Appl. Genet.*, 106:559-567, 2003; Martins M., R. et al., *Plant Cell Reports*, 22:71-78, 2003; Williams, J. G. K. et al., *Nucl. Acids Res.* 18:6531-6535, 1990; Michelmore, R. W., et al., *Proc. Natl. Acad. Sci.* USA. 88:9828-9832, 1991; Martins et al., *Plant Cell Rep.*, 22:71-79, 2003; Orita et al., *Proc. Natl. Acad. Sci.* USA 86:2766-2770, 1989). Preferably, the detection method may be performed by the RFLP, RAPD or CAPS analysis.

Concretely, the detection method may be performed by the CAPS analysis comprising the steps of:
(a) performing PCR on each of genomic DNA templates obtained from CMV-resistant plants and CMV-susceptible plants, using a primer comprising a series of nucleotides selected from the nucleotide sequence set forth in SEQ ID NO. 2 or SEQ ID NO: 22;
(b) digesting the PCR product with a restriction enzyme;
(c) electrophoresing the digested DNA fragments on agarose gel; and
(d) performing the comparison between the DNA band patterns of the electrophorsed gel.

The primer in the step (a) may preferably be selected from the group consisting of SEQ ID NO. 23 to SEQ ID NO: 28. Preferably, a primer combination selected from the group consisting of a combination of SEQ ID NO: 23 and SEQ ID NO: 24, a combination of SEQ ID NO: 23 and SEQ ID NO: 25, a combination of SEQ ID NO: 23 and SEQ ID NO: 26, and a combination of SEQ ID NO: 27 and SEQ ID NO: 28, may be used. Furthermore, as the restriction enzyme in the step (b), any restriction enzyme present in the nucleotide sequence set forth in SEQ ID NO: 2 or SEQ ID NO: 22 may be used without limitations, and preferably, XbaI or EcoRI may be used.

Moreover, the detection method may also be performed by the RAPD analysis comprising the steps of:

(a) performing PCR on each of genomic DNA templates obtained from CMV-resistant plants and CMV-susceptible plants, using a primer capable of amplifying the nucleotide sequence set forth in SEQ ID NO: 2;
(b) electrophoresing the PCR products on agarose gel; and
(c) performing the comparison between the DNA band patterns of the electrophoresed gel.

The primer in the step (a) may have all nucleotide sequences which can be designed by a person skilled in the art so as to amplify the nucleic acid set forth in SEQ ID NO: 2. Preferably, the primer may have a nucleotide sequence set forth in SEQ ID NO: 1.

In addition, the detection method may also be performed by the RFLP analysis comprising the steps of:
(a) digesting each of genomic DNA templates obtained from CMV-resistant plants and CMV-susceptible plants with a suitable restriction enzyme;
(b) electrophoresing the digested DNA fragments on agarose gel;
(c) transferring the DNA-containing gel to a nylon membrane;
(d) performing Southern blot analysis for the gel using the nucleic acid having the nucleotide sequence set forth in SEQ ID NO: 2 as a probe; and
(e) exposing the gel onto an X-ray film to perform the comparison between the DNA band patterns of the gel.

As the restriction enzyme in this method, any restriction enzyme known in the art may be used without limitations, and preferably a restriction enzyme causing DNA polymorphism may be used. More preferably, an enzyme selected from the group consisting of EcoRI, EcoRV and XbaI may be used.

Also, the inventive molecular marker may be used to determine the genotype of the CMV-resistant plant. Thus, the present invention provides a method for determining the genotype of a CMV-resistant plant, which comprises analyzing the genomic DNA of a plant in the presence of the inventive nucleic acid or primer. This method may be performed by various DNA polymorphism analyses known in the art. Concretely, this method is performed as described for the method for detecting the CMV-resistant plants.

The plant to which the inventive methods may be applied includes, but is not limited to, cucumber, watermelon, red pepper, melon, Chinese cabbage, tobacco, Petunia, cotton, and rose.

Moreover, the present invention provides a kit for the detection of a CMV-resistant plant, which comprises either a nucleic acid consisting of the nucleotide sequence set forth in SEQ ID NO: 2 or SEQ ID NO: 22, or a series of nucleotides selected from the nucleotide sequence of the nucleic acid. The inventive kit may additionally comprise various reagents required not only in test procedures (PCR, Southern blot analysis, etc) to detect CMV-resistant plants using the above nucleic acid or primer but also in a procedure to examine the test results. For example, the inventive kit may additionally comprise PCR reaction mixture, restriction enzyme, agarose, buffer required for hybridization and/or electrophoresis, etc.

Furthermore, the present invention provides a CMV-resistant plant which comprises a nucleic acid consisting of the nucleotide sequence set forth in SEQ ID NO: 2 or SEQ ID NO: 22, the nucleic acid being a molecular marker having a close association with the CMV resistant character of plants. As used herein, the term "a CMV-resistant plant" refers to the plant showing a character of resistance to CMV. The plant includes, but is not limited to, cucumber, watermelon, red pepper, melon, Chinese cabbage, tobacco, Petunia, cotton and rose. The red pepper is preferable. Also, the CMV-resistant plant provided in the present invention includes the organ, tissue, cell, seed and callus of plants. Tests on whether the CMV resistance of the inventive CMV-resistant plants is hereditary were performed, and the test results proved that the CMV resistance is determined by a dominant single gene. The inventive CMV-resistant plant can reproduce asexually by a general tissue culture method known in the art. For example, the inventive plant can reproduce asexually by fine reproduction by organ generation (e.g., a method of culturing tissue, such as leaves having no organ formed therein, leaves, petioles, stem nodes, cotyledons, cotyledon axes or the like, to induce fresh shoots on the surface of the tissue) or regeneration by callus induction, and the like. In addition, the present invention provides a seed which is obtained from the CMV-resistant plant and comprises the nucleic acid consisting of the nucleotide sequence set forth in SEQ ID NO: 2 or SEQ ID NO: 22.

BEST MODE FOR CARRYING OUT THE INVENTION

Figure 1:
FIG. 1 is a photograph showing the results of RAPD analysis performed using operon primers (OPC-04 to OPC-08 and OPC-10) and using CMV-resistant DNA pool (R) or CMV-susceptible DNA pool (S) as templates.

Hereinafter, the present invention will be described in further detail by the following examples. It is to be understood, however, that these examples are given for illustrative purpose only and are not intended to limit the scope of the present invention.

Example 1

Construction of Crossed Population for Molecular Marker Development of CMV-Resistant Red Pepper Plants and Examination of Hereditary Pattern of CMV Resistance CMV was inoculated into a variety of red pepper plants so as to screen CMV-resistant plants. The results showed that one plant of the elgiencho lines was CMV-resistant. The screened plant was named "FP11". In order to test whether the CMV resistance of the screened FP11 is hereditary or not, a self-pollinated population and a crossed population were constructed. The crossed population was constructed by crossing the plant FP11 with FP14, a susceptible line. The crossed F1 seeds were sowed and self-pollinated to produce the F2 population, and the F2 plants were self-pollinated to produce F3 plants. The F2 and F3 populations were tested for CMV resistance, and the results showed that the CMV resistance was hereditary at a ratio of 3:1 in the F2 population, and the ratio of homo to hetero in the F3 generation was 1:2. This suggests that the CMV resistance is determined by a dominant single gene.

Example 2

DNA Isolation from Plants

DNA extraction was performed by a modification to the method of Prince, J. P., et al. (Prince, J. P., et al., *Hort Science* 32:937-939, 1997). Red pepper leaves stored at −80° C. were crushed with liquid nitrogen, and then well mixed 25 ml of DNA extraction buffer (7M urea, 0.35M sodium chloride, 0.05M Tris-HCl pH 8.0, 0.02M EDTA, 0.25% sarkosyl, 5% phenol, 0.2% sodium bisulfate). Thereafter, the mixture was introduced with 0.75 ml of 20% SDS, and incubated at 65° C. for 30 minutes while shaking at intervals of 10 minutes.

A solution of chloroform and isoamyl alcohol (24:1) was filled to the end of a 50-ml tube and well mixed for 15 minutes. The mixture solution was centrifuged at 5,000 rpm for 15 minutes, and the obtained supernatant was transferred into a fresh 50-ml tube using cheesecloth. Next, the same volume of isopropanol was added to the tube and mixed, followed by the precipitation of DNA for 1 hour. The precipitated DNA was collected using an U-shaped Pasteur pipette and placed in a 1.5-ml micro-tube to which 70% ethanol was then added to reprecipitate the DNA. The resulting DNA was dried at room temperature for 30-40 minutes. To the dried DNA pellet, 600-700 µl of TE buffer (10 mM Tris-Cl, 1 mM EDTA) was added, and the DNA solution was incubated at 65° C. for 1 hour. The culture solution was centrifuged three times. Then, the resulting DNA was transferred into a 1.5-ml tube and added with RNase (100 µg/ml) so as to remove RNA. The final concentration of the purified DNA was measured with a fluorometer.

Example 3

Selection of CMV Resistance-Associated RAPD Primer

In order to select a DNA molecular marker associated with a CMV-resistant character, RAPD (Williams, J. G. K. et al., *Nucl. Acids Res.* 18, 6531-6535, 1990) and BSA (Bulked Segregant Analysis) (Michelmore, R. W. et al., *Proc. Nat. Acad. Sci.*, 88:9828-9832, 1991) were used. Based on the CMV resistance assay results from the F2 population of Example 1, a DNA pool of 10 resistant F2 plants and a DNA pool of 10 susceptible F2 plants were prepared, respectively. The each DNA pool was controlled to a DNA concentration of 20 ng/µl. Then, the PCR was performed using the DNA as a template. In this case, for RAPD primers, about 147 primers causing a good PCR reaction were selected from about 400 primers of Operon RAPD 10-mer kits series A to series T (Operon, Alameda, Calif., USA), and the selected primers were used to probe bands showing a specific difference in amplification between the resistant DNA pool and the susceptible DNA pool.

The PCR reaction mixture consisted of a 25-μl total volume of 1×PCR buffer, 60 ng of the template DNA, 0.3 mM dNTP, 0.6 pM primer, 3.5 mM MgCl$_2$, and 0.6 Unit Taq DNA polymerase (Takara, Japan). The PCR amplification consisted of the following: denaturation of template DNA of 4 minutes at 94° C.; 45 cycles each consisting of 1 minute at 94° C., 1 minute and 30 seconds at 36° C., and 1 minute and 50 seconds at 72° C.; and final extension of 5 minutes at 72° C. As a result, as shown in FIG. 1, a molecular marker which had show specificity only to the resistant pool in the PCR reaction with an OPC-07 primer (SEQ ID NO: 1) was selected.

Figure 2A:
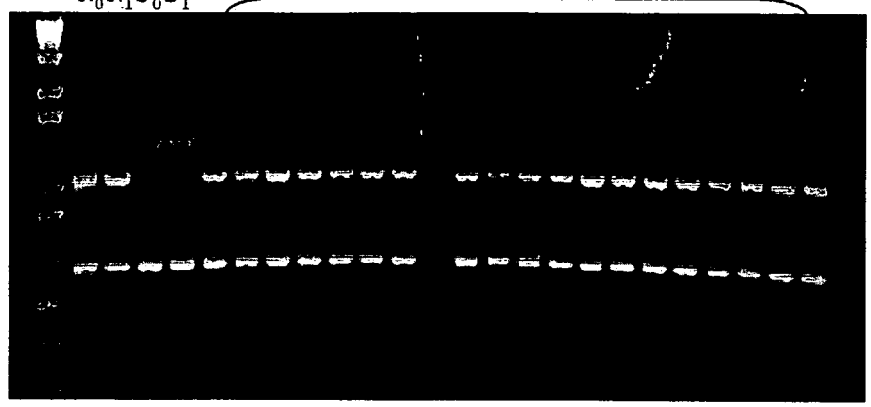
FIGS. 2a and 2b are photographs showing the results of RAPD analysis performed for resistant plants ($R_0$) and their F1 ($R_1$), susceptible plants ($S_0$) and their F2 ($S_1$), resistant plants F2 and susceptible plants F2, using an OPC-07 primer (SEQ ID NO: 1).
Figure 2A:
Figure 2B:
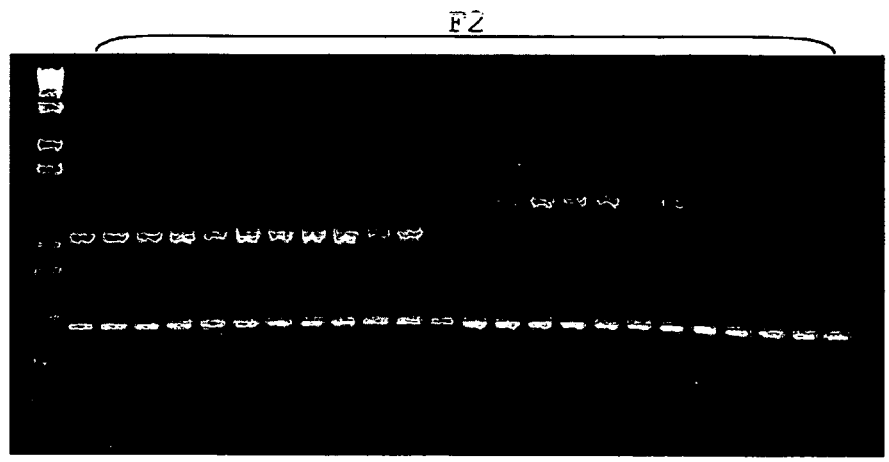
Figure 2B:
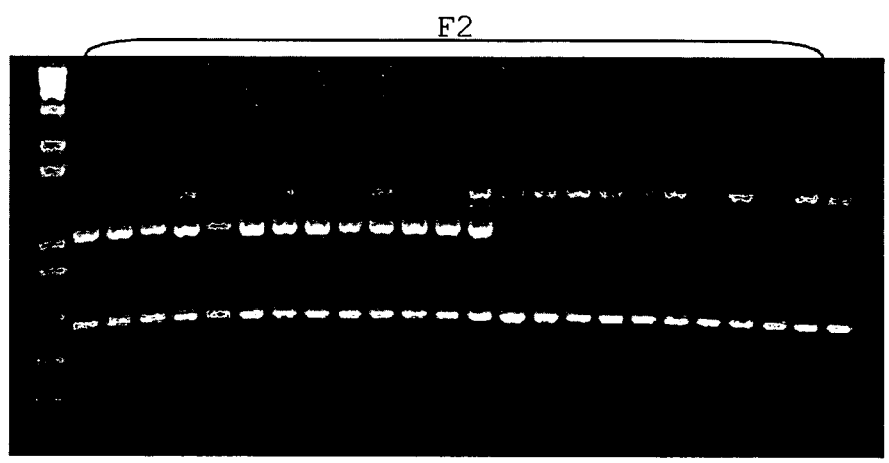

In order to examine whether the molecular marker is linkaged to a CMV-resistant character, RAPD analysis was further performed on a resistant plant and a susceptible plant and their F1 generation, and 183 resistant F2 plants and 64 susceptible F2 plants. As shown in FIGS. 2a and 2b, the analysis results showed that the molecular marker was 100% co-segregated.

Example 4

Cloning and Nucleotide Sequence Determination of RAPD Molecular Marker

The DNA amplified with the OPC-07 primer (10 mer) having a nucleotide sequence set forth in SEQ ID NO: 1 was isolated and purified from gel, and cloned into a pGEM-T vector (Promega). The cloned plasmid was introduced into *E. coli* DH 10B by electroporation, and transformants were screened in an antibiotic-containing medium. Recombinant plasmids were isolated from the screened transformants, and the nucleotide sequences of DNAs contained in the plasmids were analyzed. The determined nucleotide sequences are set forth in SEQ ID NO: 2.

Example 5

Figure 3:
FIG. 3 shows the results of RFLP analysis performed using a DNA fragment (SEQ ID NO: 2) amplified by an OPC-07 primer as a probe.
R: resistant plants
S: susceptible plants

Southern Blot Analysis for Inverse PCR and Conversion into CAPS Molecular Marker The genomic DNA of each of resistant plants and susceptible plants was prepared, and digested with DNA restriction enzymes, EcoRV, HindIII, XbaI and EcoRI, respectively. The digested DNA was electrophoresed on agarose gel. The DNA was transferred to a nylon membrane and then subjected to Southern blot analysis using a CMV-resistant specific DNA probe (SEQ ID NO: 2) amplified in Example 4. The analysis results are shown in FIG. 3. As shown in FIG. 3, DNA polymorphism was shown for EcoRI, XbaI, EcoRV but was not shown for HindIII. Based on the RFLP analysis results, EcoRI, XbaI and EcoRV restriction enzymes were used for inverse PCR and conversion into a CAPS molecular marker.

Example 6

Determination of Nucleotide Sequence of DNA Close to CMV-Resistant Gene

Based on the results of Example 5 shown in FIG. 3, the parts of the nucleotide sequence of the RAPD molecular marker analyzed in Example 4 were used to construct primers. The nucleotide sequence of each of the constructed primers is given in Table 1 below.

TABLE 1

Primers used in inverse PCR

| Primer name | Nucleotide sequence (5'→3') | SEQ ID NO |
|---|---|---|
| CRSCC07a | GTC CCG ACG ATA GCC CAA AAG | 3 |
| CRINVR65 | TTG GCC CTA TGA GTC CGT AC | 4 |
| CRINVR125 | ACT GAC TAC GAG TTG TCA CC | 5 |
| CRINVF629 | TAG GGG TTC AAG GAT CAC CC | 6 |
| CRINVR796 | TAT CCT CTT ATG CAA TGC GC | 7 |
| CRINVR840 | AAT CCT TGT ACC TCA CAA CG | 8 |
| CRINVF975 | CGA TGC CAC TTC ATA ATG CC | 9 |
| Inv 1030514 R | GAC TTG GGC ACT ACA CTG GA | 10 |
| Inv 1030514 F | ACA TAG GCG TGT GCT CTG GA | 11 |
| CR1541-3 | GGA GTT TCA TCA TAT GAA GCC | 12 |
| InvXbTopF1010 | GGT TCA AGG ATC ACC CAA ATA A | 13 |
| InvXbTopR107 | TTC ACC TTA GTC CCC AAA CCT A | 14 |
| EV Inver F2 | AAC CCA AGC CTA TTT TAG CC | 15 |
| EV-INV-XbaI | GGT AAT AGG GTT CAC CTT AGT C | 16 |
| CRINVF5095 | CTT TGA GCC AAA GAA TGG AA | 17 |
| CRINVR4776 | TTT GGT AAT GAC CGG AGA CC | 18 |
| INVER0827R | ATA GCA GAG GAG CAC CCT AC | 19 |
| INVER0827F1 | GGT ACA AGG ATT CCC CAA AGT G | 20 |
| INVER0827F2 | GAT TTA GTC AGT ATG ACG ATG CCA C | 21 |

The primers set forth in Table 1 above were used to perform inverse PCR on resistant plants according to a method known in the art (Sambrook J. and D. W. Russel. 2001. Molecular Cloning. 3rd ed., Cold Spring Harbor Laboratory Press, Cold Spring Harbor, N.Y.).

First, the genomic DNA digested with HindIII was circularly ligated with T7 DNA ligase. The ligated DNA template was then amplified by PCR with a primer combination Of SEQ ID NO: 5 and SEQ ID NO: 6. The PCR product was reamplified by nested PCR using a primer combination of SEQ ID NO: 4 and SEQ ID NO: 9, thus obtaining a PCR product with about 900-bp size. The nucleotide sequence of the PCR product was analyzed by a primer walking method. The nucleotide sequence was linked to a nucleotide sequence of SEQ ID NO: 2, thus obtaining a 1.8-kb nucleotide sequence having HindIII sites at both ends. Thereafter, based on the 1.8-kb nucleotide sequence, primers of SEQ ID NO: 10 and SEQ ID NO: 11 were constructed. The primer combination of SEQ ID NO: 10 and SEQ ID NO: 11 was used to perform inverse PCR using a genomic DNA template which had been digested with EcoRV and circularly ligated. The nucleotide sequence of the PCR product was linked to the 1.8-bp nucleotide sequence, thus obtaining a 3.4-kb nucleotide sequence having EcoRV sites at both ends. Similarly, a genomic DNA template which had been digested with XbaI and circularly ligated was subjected to inverse PCR with primers of SEQ ID NO: 13 and SEQ ID NO: 14. The nucleotide sequence of the PCR product was analyzed and linked to the 3.4-kb nucleotide sequence. As a result, a nucleotide sequence with about 5.6-kb length containing a nucleotide sequence of SEQ ID NO: 2 was determined. This nucleotide sequence is set forth in SEQ ID NO: 22.

Example 7

Conversion into CAPS Molecular Marker

After finding out the DNA restriction enzyme site of DNA nucleotide sequences known in the nucleotide sequences of SEQ ID NO: 22, the restriction enzyme site of genomic DNA of resistant plants was compared with that of susceptible plants. Then, XbaI (T'CTAG_A), EcoRI (G'AATT_C) and EcoRV (GAT'ATC), which are restriction enzymes showing the polymorphism between the two genomic DNAs, were selected as enzymes to be used in CAPS. Then, primers capable of amplifying DNA fragments showing a restriction pattern with suitable length. Namely, 4 primers each consisting of a series of nucleotide sequences selected from the nucleotide sequences set forth in SEQ ID NO: 22 were constructed (see Table 2 below).

TABLE 2

Primers for development of CAPS molecular marker for examination of CMV resistance

| No | Nucleotide sequence (5'→3') | Primer name | Direction | SEQ ID NO |
|---|---|---|---|---|
| 1 | GTAGTAGGGTACGGACTCATA | SCC07S3 | Forward | 23 |
| 2 | GTCCCGACGATAGCCCAAAAG | SCC07a | Reverse | 24 |
| 3 | GGAGTTTCATCATATGAAGCC | CR1541-3 | Reverse | 25 |
| 4 | AGTGGAGCTTGGGGTAGTCC | FP5416R | Reverse | 26 |

The genomic DNA was extracted from a resistant plant, a susceptible plant and their F2 population, respectively, and used as a template for PCR. The PCR was performed with the DNA template and a primer combination of SEQ ID NO: 23 and SEQ ID NO: 24, a primer combination of SEQ ID NO: 23 and 25, and a combination of SEQ ID NO: 23 and 26, respectively. The PCR amplification consisted of the following: initial denaturation of template DNA of 1 minute at 94° C.; 35 cycles each consisting of 1 minute at 94° C., 1 minute at 58° C., and 2 minutes at 72° C.; and final extension of 10 minute at 72° C. Thereafter, each of the amplified DNAs was digested with restriction enzymes (EcoRI, XbaI, EcoRV) selected in Example 6, and electrophoresed on agarose gel so as to examine if the DNA was divided into genotypes, i.e., homo (RR) and hetero (Rr).

Figure 4:
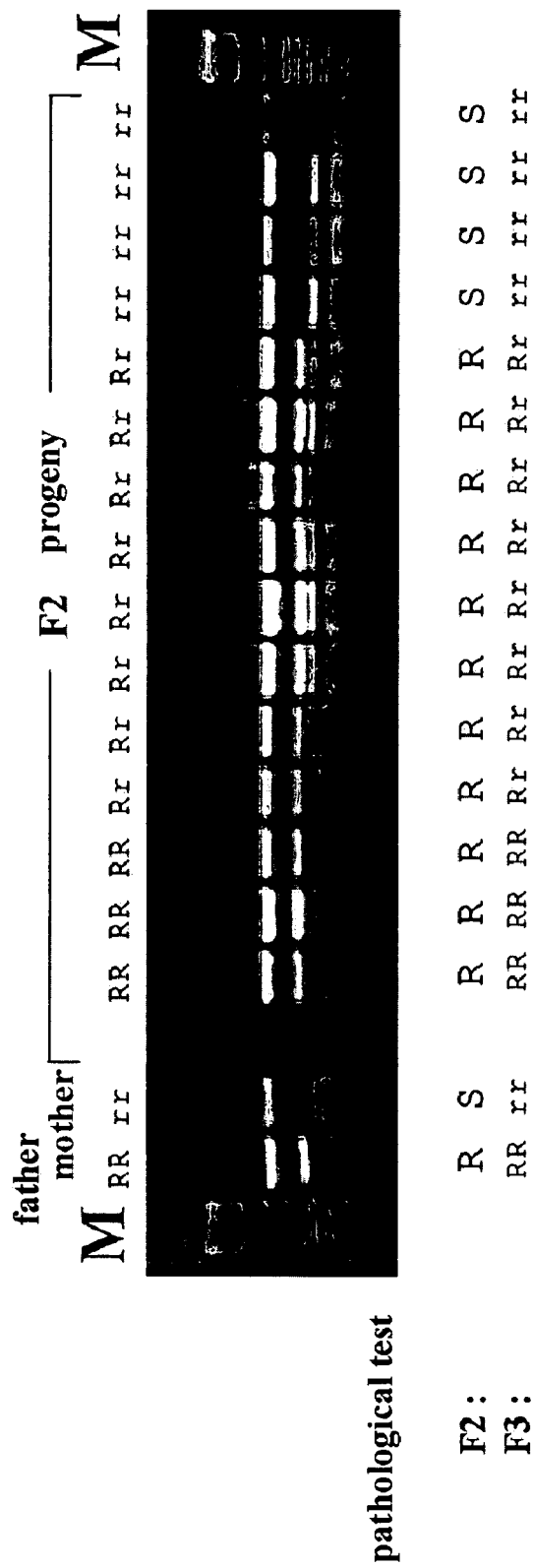
FIG. 4 is a photograph showing the results of CAPS analysis performed using primers of SEQ ID NO: 23 and SEQ ID NO: 24.

The results of the PCR amplification performed with the primer combination of SEQ ID NO: 23 and SEQ ID NO: 24 are shown in FIG. 4. The PCR-amplified DNA fragment was 1.0 kb in size. The PCR-amplified DNA fragment was digested with XbaI, and the result showed that the band patterns of the susceptible and resistant plants were different from each other. Also, it could be fount that these band patterns were co-segregated with the genotype of the F2 plants, which had been expected by testing the disease resistance of F3 in Example 1.

Figure 5:
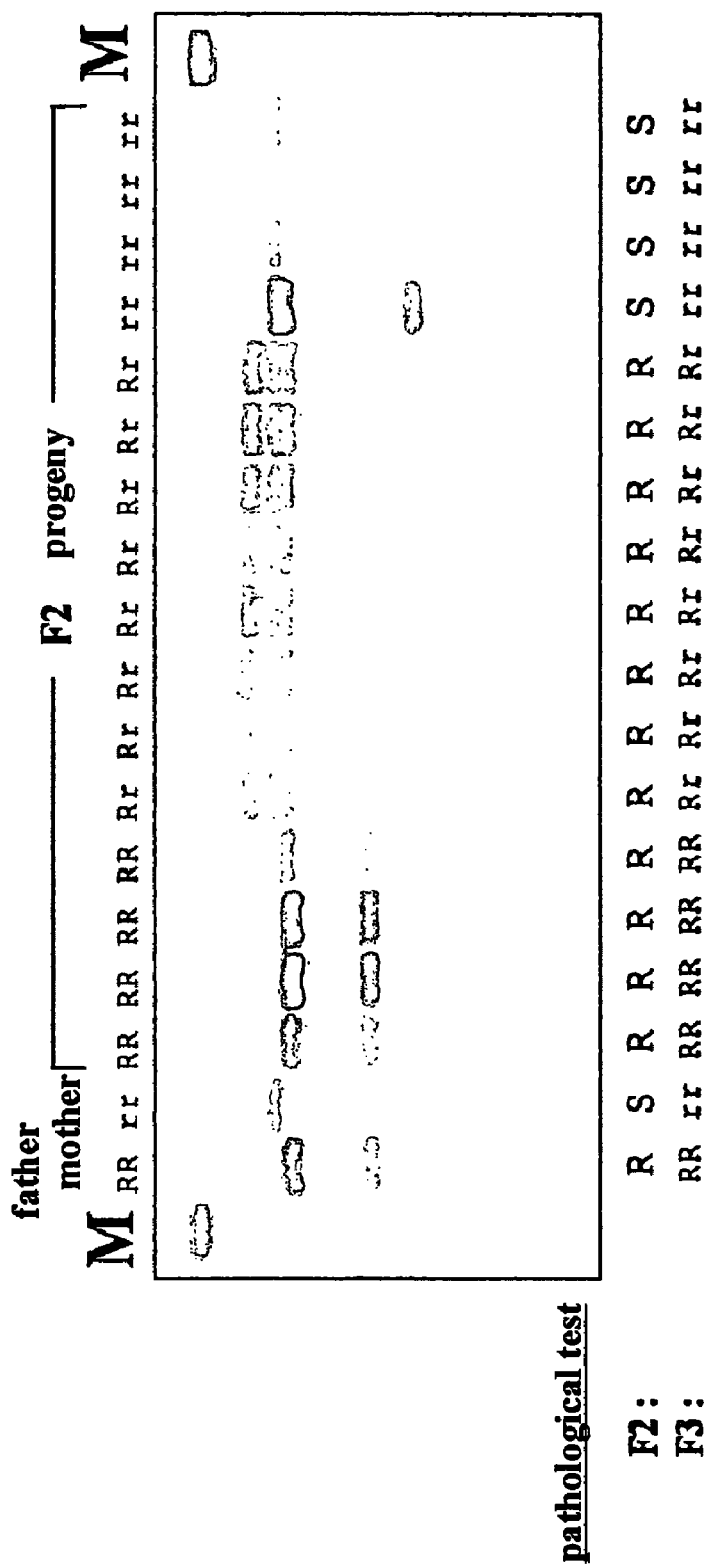
FIG. 5 is a photograph showing the results of CAPS analysis performed using a primer combination of SEQ ID NO: 23 and SEQ ID NO: 25.
A: digested with EcoRI
B: digested with XbaI

The results of the PCR amplification performed with the primer combination of SEQ ID NO: 23 and SEQ ID NO: 25 are shown in FIG. 5. The PCR-amplified DNA fragment was 1,477 bp in size. The amplified DNA fragment was digested with each of EcoRI (A) and XbaI (B), and the results showed that the band patterns of the susceptible and resistant plants were different from each other. Also, it could be fount that these band patterns were co-segregated with the disease resistance results shown in Example 1.

Figure 6:
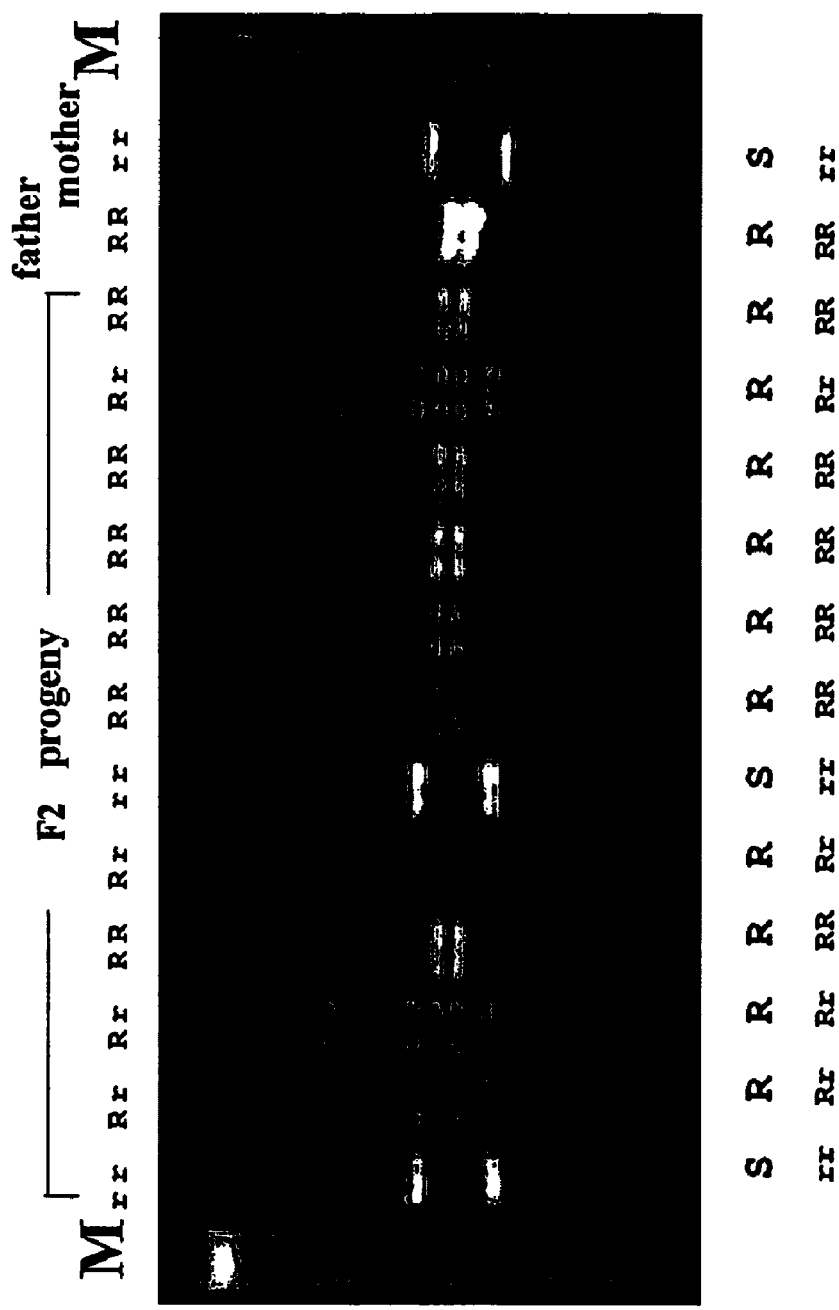
FIG. 6 is a photograph showing the results of CAPS analysis performed using a primer combination of SEQ ID NO: 23 and SEQ ID NO: 26.

The results of the PCR amplification performed with the primer combination of SEQ ID NO: 23 and SEQ ID NO: 26 are shown in FIG. 6. The PCR-amplified DNA fragment was 1,846 bp in size. The amplified DNA fragment was digested with EcoRI, and the results showed that the band patterns of the susceptible and resistant plants were different from each other. Also, it could be found that these band patterns were co-segregated with the disease resistance results shown in Example 1.

The above results show that, if a primer constructed from a series of any nucleotides selected from the nucleotide sequences set forth in SEQ ID NO: 22 is used to perform PCR and the resulting PCR product is digested with the restriction enzyme present in SEQ ID NO: 22, the presence or absence of a CMV-resistant gene and its genotype (i.e., homo or hetero) can be determined. Namely, since the nucleotide sequences set forth in SEQ ID NO: 22 significantly approach to CMV-resistant genes, the use of any polymorphism shown by the nucleotide sequences allows the presence or absence of CMV-resistant genes to be determined.

Example 8

Figure 7:
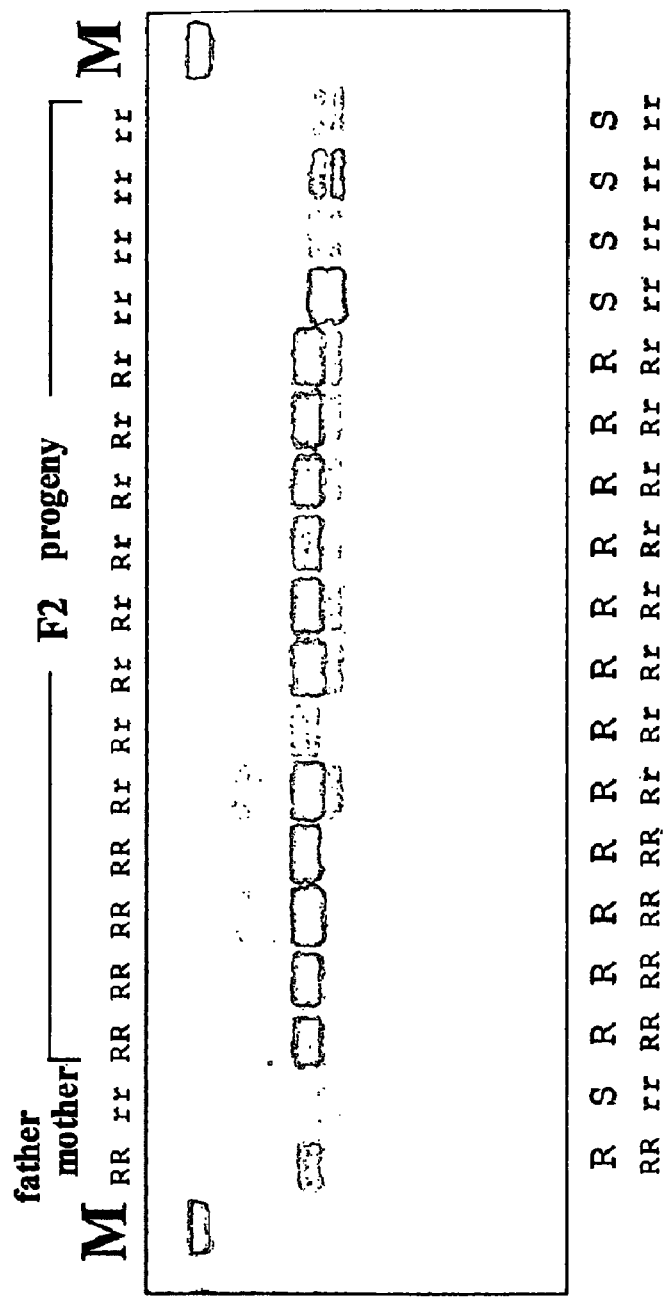
FIG. 7 is a photograph showing the results of CAPS analysis performed using a primer combination of SEQ ID NO: 27 and SEQ ID NO: 28.

Determination of Smallest Number of Consecutive Nucleotides which can be Converted into CAPS Molecular Markers The following test was performed to determine the smallest number of nucleotide sequences convertible into a CAPS molecular marker, in the nucleotide sequences of SEQ ID NO: 22 determined in Example 6. For this purpose, a nucleotide sequence of SEQ ID NO: 23 (forward [SCC07S3]: 5'-GTAGTAGGGTACGGACTCATA-3') was modified with a nucleotide sequence of SEQ ID NO: 27 (forward [SCC07S3-change]: 5'-gGTAGTAGGGTACG-3'), and a nucleotide sequence of SEQ ID NO: 25 (Reverse [CR1541-3]: 5'-GGAGTTTCATCATATGAAGCC-3') was modified with a nucleotide sequence of SEQ ID NO: 28 (Reverse [CR1541-3-change]: 5'-gGGAGTTTCATCAgc-3'). Here, the small letters represent any deletion or substitution. The modified primers of SEQ ID NO: 27 and SEQ ID NO: 28 were used to perform PCR amplification. The PCR amplification consisted of the following: initial denaturation of template DNA for 1 minute at 94° C.; 40 cycles each consisting of 1 minute at 94° C., 1 minute at 50, 52, 54, 56 or 58° C., and 2 minutes at 72° C.; and final extension of 10 minutes at 72° C. The amplified DNA fragment was 1,477 bp in size. Thereafter, the amplified DNA was digested with EcoRI and electrophoresed on agarose gel. As shown in FIG. 7, the electrophoresis results showed that the band patterns of the susceptible and resistant plants were different from each other and co-segregated with the disease resistance results shown in Example 1.

The above results suggest that the primer obtained by modifying at least 12 consecutive nucleotides selected from the nucleotide sequences set forth in SEQ ID NO: 22 is also useful as a CAPS marker for detecting the CMV resistance.

INDUSTRIAL APPLICABILITY

As described above, the present invention provides the molecular marker which comprises the nucleotide sequence highly linkaged to the CMV-resistance, such that CMV-resistant plants can be effectively diagnosed with little or no diagnostic error. Moreover, the inventive molecular marker and the detection method using the same can detect CMV-resistant plants in a rapid and precise manner without inoculating CMV directly into plants, and also can determine the genotype of CMV-resistant plants.

What is claimed is:

1. An isolated nucleic acid consisting of the nucleotide sequence set forth in SEQ ID NO: 2 or SEQ ID NO: 22.

2. An isolated nucleic acid of claim 1 further comprising a primer for the detection of a CMV-resistant plant, which comprises a consecutive nucleotide selected from a nucleotide sequence set forth in SEQ ID NO: 23 to SEQ ID NO: 28.

3. A kit for the detection of CMV-resistant plant, which comprises the nucleic acid of claim 1.

4. A method for the detection of a CMV-resistant plant, comprising the step of analyzing the genomic DNA of a plant in the presence of the nucleic acid of claim 1.

5. The method of claim 4, wherein the analysis is performed by any one method selected from the group consisting of RFLP (restriction fragment length polymorphism), RAPD (randomly amplified polymorphic DNA), DAF (DNA amplification fingerprinting), AP-PCR (arbitrarily primed PCR), STS (sequence tagged site), EST (expressed sequence tag), SCAR (sequence characterized amplified regions), ISSR (inter-simple sequence repeat amplification), AFLP (amplified fragment length polymorphism), CAPS (cleaved amplified polymorphic sequence) and PCR-SSCP (PCR-single strand conformation polymorphism).

6. The method of claim 4, wherein the plant is selected from the group consisting of cucumber, watermelon, red pepper, melon, Chinese cabbage, tobacco, Petunia, cotton, and rose.

7. A method for determining the genotype of a CMV-resistant plant, comprising the step of analyzing the genomic DNA of a plant in the presence of the nucleic acid of claim 1.

8. The method of claim 7, wherein the analysis is performed by any one method selected from the group consisting of RFLP (restriction fragment length polymorphism), RAPD (randomly amplified polymorphic DNA), DAF (DNA amplification fingerprinting), AP-PCR (arbitrarily primed PCR), STS (sequence tagged site), EST (expressed sequence tag), SCAR (sequence characterized amplified regions), ISSR (inter-simple sequence repeat amplification), AFLP (amplified fragment length polymorphism), CAPS (cleaved amplified polymorphic sequence), and PCR-SSCP (PCR-single strand conformation polymorphism).

9. The method of claim 7, wherein the plant is selected from the group consisting of cucumber, watermelon, red pepper, melon, Chinese cabbage, tobacco, Petunia, cotton, and rose.

10. A CMV-resistant plant which reproduces asexually by tissue culture and comprises a nucleic acid consisting of a nucleotide sequence set forth in SEQ ID NO: 2 or SEQ ID NO: 22.

11. The CMV-resistant plant of claim 10, wherein the plant is selected from the group consisting of cucumber, watermelon, red pepper, melon, Chinese cabbage, tobacco, Petunia, cotton, and rose.

12. A seed which is obtained from the CMV-resistant plant of claim 10 and comprises a nucleic acid consisting of a nucleotide sequence set forth in SEQ ID NO: 2 or SEQ ID NO: 22.

13. A kit for the detection of CMV-resistant plant, which comprises the isolated nucleic acid of claim 2.

14. A seed which is obtained from the CMV-resistant plant of claim 11 and comprises a nucleic acid consisting of a nucleotide sequence set forth in SEQ ID NO: 2 or SEQ ID NO: 22.

* * * * *